United States Patent [19]

Huber

[11] Patent Number: Plant 5,834

[45] Date of Patent: Dec. 16, 1986

[54] *SPIRAEA×BUMALDA* CV. MONHUB'

[75] Inventor: Tony Huber, Laval, Canada

[73] Assignee: Monrovia Nursery Company, Azusa, Calif.

[21] Appl. No.: 688,443

[22] Filed: Dec. 31, 1984

[51] Int. Cl.[4] ..... A01H 5/00
[52] U.S. Cl. ..... Plt./54
[58] Field of Search ..... Plt./54

*Primary Examiner*—Robert E. Bagwill

[57] ABSTRACT

A new and distinct selection of *Spiraea×bumalda* (Burv.) shrub (popularly known as Spiraea) which shall be referred to hereinafter as *Spiraea×bumalda* cultivar Monhub. *Spiraea×bumalda* cultivar Monhub differs from other Spiraeas by a combination of attributes of mature foliage a lemon-green color, juvenile foliage yellow with russet new growth, autumn foliage a salmon russet color, light pink flowers, a dense, compact, uniform growth and a tolerance of temperature to minus 42° F.

2 Drawing Figures

DISCOVERY

This invention relates to a new distinct selection of *Spiraea×bumalda,* a member of the Rose family, Rosaceae. *Spiraea×bumalda* cv. Monhub was a result of direct hybridizing in 1978. The parents are one of my selections hybridized with *Spiraea×bumalda* 'Goldflame'. In September of 1979 the selection was made at W. H. Perron Nursery, Quebec, Canada.

The plant to date exists only within the boundaries of W. H. Perron Nursery, Quebec, Canada and Monrovia Nursery Company, Azusa, Calif. This selection has not been offered for sale or described in any publication.

REPRODUCTION

This new selection has been strictly asexually reproduced by softwood cuttings at W. H. Perron Nursery in order to retain the characteristics of lemon-green mature foliage, yellow juvenile foliage with russet new growth, autumn foliage a salmon russet color, the light pink flowers, the dense compact uniform growth habit and the cold hardiness. Sexual reproduction, such as seed propagation, could result in a potential loss of these selected attributes. Therefore, sexual reproduction is prohibited and propagation is restricted to asexual reproduction by cuttings. Seed progeny from the new selection has not been observed.

CHARACTERISTICS

*Spiraea×bumalda* 'Monhub' differs from other selections known to exist by posessing a combination of unique characteristics listed below:

(1) The mature foliage color of my new selection is a lemon-green (Scheeles Green 860/1). *Spiraea×bumalda* 'Goldflame', a parent of my new selection has a mature foliage which is a darker green (Spinach Green 0960) with burgundy blotches. *Spiraea japonica* 'Alpina' and *S. japonica* 'Little Princess' when compared to my selection have a darker green foliage that is smaller in size, not at all resembling my new selection.

(2) The juvenile foliage on my selection is a yellow tone (Barium Yellow 503/1) with the new foliage exhibiting a russet color (Nasturium Red 14/1). *Spiraea×bumalda* 'Goldflame' has a juvenile foliage which is a lighter shade of green not yellow and the new tips are a red-orange color (Oxblood Red 00823).

(3) In colder climates the fall foliage coloring of my new selection is unique. During the early part of autumn the overall foliage color is lemon-green color with interspersed branches of contrasting bright red. By mid-autumn the foliage turns to a salmon russet coloring before the foliage drops completely.

(4) The flowers of my selection are a light pink color arranged in flat-topped clusters and flower heavily from mid-spring through summer then sporadically in the fall. *Spiraea×bumalda* 'Goldflame' has crimson red flowers and blooms heavily in the summer months.

(5) My selection has a dense, compact habit achieving a height of 75 cm in three years. *Spiraea×bumalda* 'Goldflame' has a looser habit reaching a height of 100 cm in three years.

(6) My selection has tolerated cold temperatures to minus 42° F. without a snow cover. *Spiraea×bumalda* 'Goldflame' is recorded to take cold temperatures to minus 30° F.

BRIEF DESCRIPTION OF THE DRAWING

The above photo.

DESCRIPTION

Figure 1:
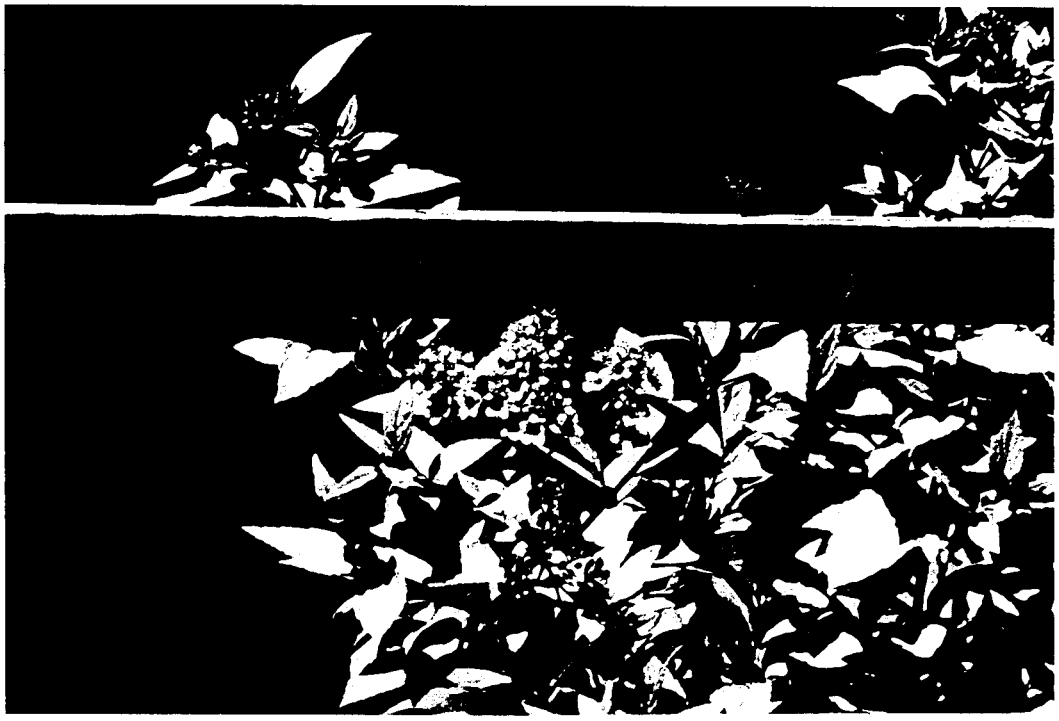
FIG. 1, labeled selection shows a close up of the foliage and flower size and exhibits the bright lemon-green color of the leaves and the light pink flowers.
Figure 2:
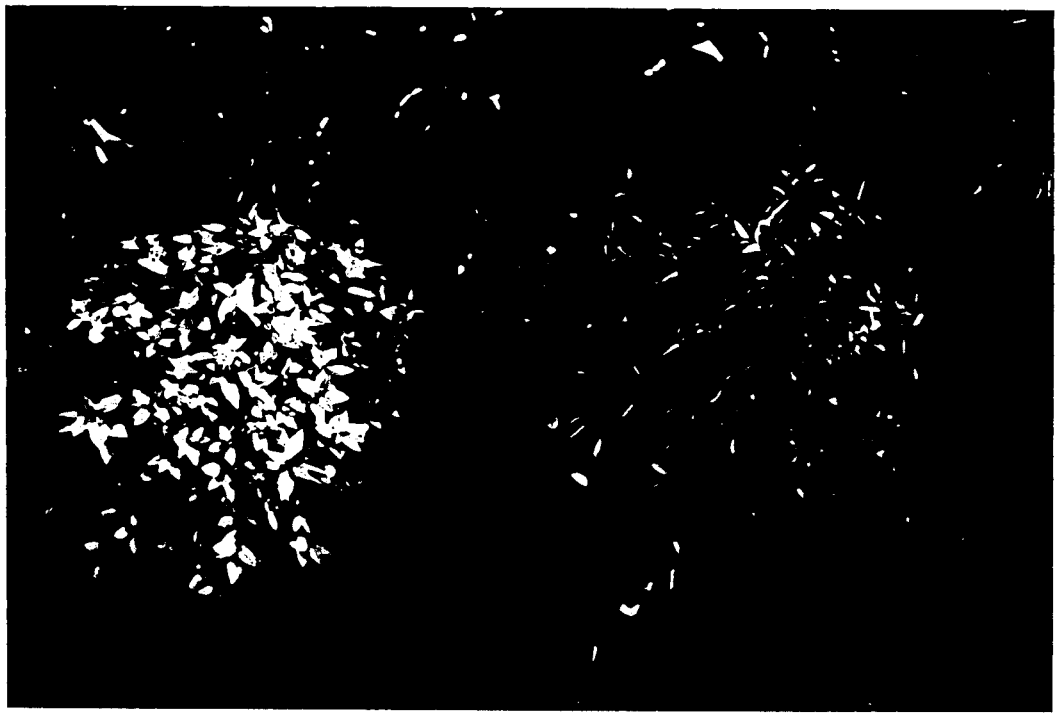
FIG. 2, the photo below, designated prior art and selection displays my selection on the left and *Spiraea×bumalda* 'Goldflame' on the right. Depicted in this photo is the compact, dense habit of my selection in contrast with the looser habit of *Spiraea×bumalda* 'Goldflame'. Also of note is the new foliage coloring and the blossom display on my selection.

Below is a detailed description of the new selection, all color terminology is derived from the British Horticultural Colour Charts:

Overall size and habit: Approximately 75 cm in height with a spread of 90 cm; habit mounding.
Inflorescence: composed of terminal corymbs.
Flowering period: Spring through Summer, flowering sporadically through out Fall.
Flower:
- *Size.*—7 mm diameter.
- *Petal shape.*—Orbicular.
- *Petal number.*—5 occasionally 4.
- *Length.*—3 mm.

*Width.*—3 mm.

*Color.*—Amaranth Rose 530/1 and Phlox Pink 625/1.

Leaf:

*Shape.*—Ovate, margins serrulate.

*Width.*—1.3 cm to 2 cm.

*Length.*—2.3 cm to 4.5 cm.

*Arrangement.*—Alternate.

*Color.*—varies from Scheeles Green 860/1 to Barium Yellow 503/1 with a tinge of Chartreuse Green 663 at leaf base and margins.

I claim:

1. A new and distinct selection of *Spiraea* × *bumalda* as substantially shown and described herein, characterized particularly as a novelty by the unique combination of mature foliage a lemon-green color, juvenile foliage yellow with russet new growth, autumn foliage a salmon russet color, light pink flowers, a dense compact uniform growth and tolerance of temperatures to minus 42° F.

* * * * *